United States Patent [19]

Gätzi

[11] 4,137,067
[45] Jan. 30, 1979

[54] PYRIDINE-4-CARBOXYLIC ACID HYDRAZIDES FOR COMBATTING PHYTOPATHOGENIC MICROORGANISMS AND FOR REGULATING PLANT GROWTH

[75] Inventor: Karl Gätzi, Basel, Switzerland

[73] Assignee: Ciba-Geigy Corporation, Ardsley, N.Y.

[21] Appl. No.: 749,864

[22] Filed: Dec. 13, 1976

Related U.S. Application Data

[63] Continuation-in-part of Ser. No. 685,594, May 12, 1976, abandoned.

[30] Foreign Application Priority Data

May 14, 1975 [CH] Switzerland .................. 06192/75
Apr. 2, 1976 [CH] Switzerland .................. 04148/76

[51] Int. Cl.² .................... A01N 9/22; C07D 213/86
[52] U.S. Cl. .................................. 71/94; 424/263;
424/266; 546/324
[58] Field of Search ............... 260/295.5 H, 295 H;
71/94; 424/263, 266

[56] References Cited

U.S. PATENT DOCUMENTS

| 2,703,322 | 3/1955 | Fox | 260/295 H |
| 3,040,061 | 6/1962 | Bloom et al. | 260/295 H |

FOREIGN PATENT DOCUMENTS

1080206 12/1954 France.
389983 7/1965 Switzerland.
711756 7/1954 United Kingdom.
729967 5/1955 United Kingdom.

OTHER PUBLICATIONS

Parravicini et al., Chem. Abstracts 84, 1976, p. 30831, parag. 30825z.
Isler et al., Fasciculus, IV (1955), No. 18, pp. 1033-1047.
Seydel et al., Congress of Chemotherapy Report.
Palat et al., Chemical Abstracts, vol. 73 (1970), 128, 151z.
Palat et al., Chemilal Abstracts, vol. 72 (1970), 55, 198n.
Isler et al., Helv. Chim Acta, vol. 38 (1955), pp. 1033-1046.
Libermann et al., Bull. Soc. Chim France (1954), pp. 1430-1443.

Primary Examiner—Richard Raymond
Attorney, Agent, or Firm—Harry Falber

[57] ABSTRACT

Compounds of formula I

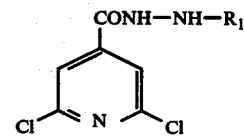

wherein
R₁ represents $C_1$-$C_4$-alkyl, alkyl($C_1$-$C_4$)-carbonyl or halogenoalkyl($C_1$-$C_3$)-carbonyl as well as salts thereof with organic and inorganic acids which are active against phytopathogenic microorganisms and in the regulation of plant growth.

18 Claims, No Drawings

PYRIDINE-4-CARBOXYLIC ACID HYDRAZIDES FOR COMBATTING PHYTOPATHOGENIC MICROORGANISMS AND FOR REGULATING PLANT GROWTH

CROSS REFERENCE

This application is a continuation in part of Ser. No. 685,594, filed May 12, 1976 and which is now abandoned.

DETAILED DISCLOSURE

The present invention relates to pyridine-4-carboxylic acid hydrazides, as well as to compositions and processes for combatting phytopathogenic microorganisms and for regulating plant growth.

The compounds of the invention correspond to formula I

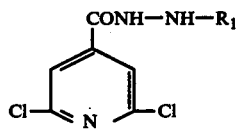

wherein
$R_1$ represents $C_1$-$C_4$-alkyl, alkyl($C_1$-$C_4$)-carbonyl or halogenoalkyl($C_1$-$C_3$)-carbonyl.

The invention also embraces salts of these compounds with organic and inorganic acids.

Pyridine-4-carboxylic acid can also be termed isonicotinic acid.

By alkyl or as alkyl-moiety of another substituent are meant, depending on the number of given carbon atoms, the following groups: methyl, ethyl, propyl or butyl as well as isomers thereof iso-propyl, iso-, sec.- or tert.-butyl.

Halogen denotes fluorine, chlorine, bromine or iodine.

Suitable salt-forming acids are, for example, hydrohalic acids, e.g. hydrochloric acid, hydrobromic acid or hydriodic acid, hydrofluoboric acid, nitric acid, phosphoric acid, thio- or dithiophosphoric acid, sulphuric acid, methanesulphonic acid, acetic acid, haloacetic acids, propionic acid, halopropionic acids, butyric acid, lactic acid, stearic acid, oxalic acid, tartaric acid, maleic acid or benzoic acid.

The compounds of formula I may be produced by one of the following schematically represented methods:

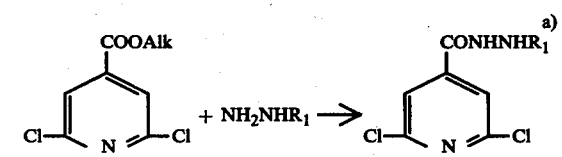

wherein
$R_1$ is as defined under formula I, and
Alk denotes alkyl, preferably methyl or ethyl;

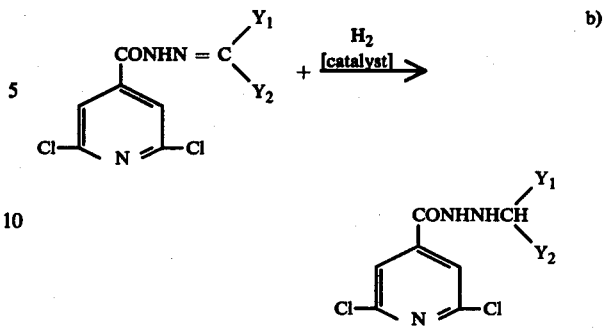

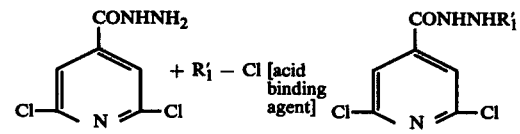

wherein
$Y_1$ is hydrogen or $C_1$-$C_3$-alkyl and
$Y_2$ is $C_1$-$C_3$ alkyl whereby
$Y_1$ and $Y_2$ together contain no more than 3 carbon atoms. (The group —CH($Y_1$)($Y_2$) corresponds to $R_1$ as $C_2$-$C_4$-alkyl);
(c) reaction with an acid chloride $R_1'$ —Cl $R_1'$ is alkyl ($C_1$-$C_4$)-carbonyl or halogenoalkyl-($C_1$-$C_3$)-carbonyl.

The aforementioned reactions may be performed in the presence or absence of solvents which are inert to the reactants and which are customarily used in such reactions. Suitable solvents are, for example: alcohols such as methanol or ethanol; ethers such as diethyl ether, dioxane or glycol monomethyl ether, as well as hydrocarbons such as benzene, toluene, petroleum ether, etc.

The remaining reaction conditions also correspond to those of similar known processes e.g.:
for
(a) temperatures of between 0° and 100° C., preferably between 60° and 80° C.; and normal pressure;
(b) temperatures of between 10° and 30° C., preferably between 15° and 20° C.; presence of a noble-metal catalyst, such as platinised charcoal (5%) or an analogous rhodium catalyst; and normal or low pressure;
(c) presence of an acid-binding agent, such as an alkali metal hydroxide or alkaline-earth metal hydroxide or an alkali metal carbonate or alkaline-earth metal carbonate; bases such as triethylamine, N,N-dimethylaniline or pyridine; temperatures of between 0° and 50° C.; preferably between 10° and 30° C.; and normal pressure.

The salts may also be produced by methods known per se. Compounds similar to those of the instant invention are described in BULL.SOC.CHIM.FRANCE (1954) pp 1430-43 and HELV.CHIM.ACTA 38 pp 1033-46 (1955).

The compounds of formula I can be used for combatting various phytopathogenic microorganisms. Thus, for example, some of the compounds of formula I are effective against phytopathogenic fungi. In particular, however, they are suitable for controlling phytopathogenic bacteria.

The term phytopathogenic fungi embraces, for example, fungi of the genera Phytophthora or Venturia.

As phytopathogenic bacteria, there can be mentioned, inter alia, members of the genera Pseudomonas, e.g. *Pseudomonas tomato, Pseudomonas lachrymans, Pseudomonas phaseolicola, Pseudomonas tabaci* and *Pseudomonas syringae*, Xanthomonas, e.g. *Xanthomonas oryzae, Xanthomonas vesicatoria, Xanthomonas phaseoli, Xanthomonas campestri* and *Xanthomonas citri*, as well as Erwinia and Corynebacterium.

A special property of the compounds of formula I is their systemic action against phytopathogenic parasites, i.e. their ability to undergo translocation in a plant to a site of infection that is remote from the point of application. After treatment of the soil, such a compound can thus be absorbed by the roots of a plant and conveyed to the site of infection.

The compounds can be used on useful crops such as cereals, maize, potatoes, rice, vegetables, grape vines, ornamental plants, fruit, and so forth.

A number of the compounds of formula I possess the property of advantageously regulating or modifying plant growth. It is thus possible, inter alia, to prevent therewith excessive undesirable growth, such as grasses along the verges of highways, on river banks, etc., or of side shoots (suckers) on tobacco plants.

The compounds of formula I may also be used to influence the abscission of various fruits, particularly of citrus fruits.

In order to adapt them to suit given circumstances and also to broaden their sphere of action, the compounds of formula I may be used together with other suitable pesticides, such as bactericides, fungicides, insecticides or acaricides, or with other active substances influencing plant growth.

The compounds of formula I can be used on their own or together with suitable carriers and/or additives. Suitable carriers and additives may be solid or liquid, and correspond to substances common in formulation practice, such as natural or regenerated mineral substances, solvents, dispersing agents, wetting agents, adhesives, thickeners, binders or fertilisers. Such compositions are produced in a manner known per se by the intimate mixing and grinding of their constituent parts.

For application, the compounds of formula I can be used in the following forms:

Solid Preparations
  dusts, scattering agents, granulates (coated granulates, impregnated granulates and homogeneous granulates) or pellets;

Liquid Preparations
  (a) water-dispersible active-substance concentrates: wettable powders, pastes and emulsions; solution concentrates;
  (b) solutions: aerosols.

The content of active substance in the above-described compositions is between 0.1 and 95% by weight. The active substances of formula I can be formulated, e.g., as follows:

Dusts

The following substances are used in the preparation of (a) a 5% dust and (b) a 2% dust:

| | | |
|---|---|---|
| a) | 5 | parts of Active Substance, |
| | 95 | parts of talcum; |
| b) | 2 | parts of Active Substance; |
| | 1 | part of highly dispersed silicic acid, |
| | 97 | parts of talcum. |

The active substances are mixed and ground with the carriers and can be applied in this form by dusting.

Granulates

The following substances are used to produce a 5% granulate:

5 parts of Active Substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin, and the mixture is dissolved in 6 parts of acetone; the polyethylene glycol and cetyl polyglycol ether are then added. The solution obtained in this manner is sprayed onto kaolin and the acetone subsequently evaporated off in vacuo. A microgranulate of this kind is particularly suitable for application to the soil.

Wettable powders

The following constituents are used to produce (a) a 70%, (b) a 40%, (c) and (d) a 25% and (e) a 10% wettable powder:

| | | |
|---|---|---|
| a) | 70 | parts of Active Substance, |
| | 5 | parts of sodium dibutyl-naphthalene sulphonate, |
| | 3 | parts of naphthalenesulphonic acid/phenolsulphonic acid/formaldehyde condensate 3:2:1, |
| | 10 | parts of kaolin, |
| | 12 | parts of Champagne chalk; |
| b) | 40 | parts of Active Substance, |
| | 5 | parts of sodium lignin sulphonate, |
| | 1 | part of sodium dibutyl-naphthalene sulphonate, |
| | 54 | parts of silicic acid; |
| c) | 25 | parts of N-(2,6-dichloropyridine-4-carboxylic acid)-N'-sec-butyl-hydrazide, |
| | 4.5 | parts of calcium lignin sulphonate, |
| | 1.9 | parts of Champagne chalk/hydroxyethyl cellulose mixture (1:1), |
| | 1.5 | parts of sodium dibutyl naphthalene sulphonate, |
| | 19.5 | parts of silicic acid, |
| | 19.5 | parts of Champagne chalk, |
| | 28.1 | parts of kaolin; |
| d) | 25 | parts of Active Substance, |
| | 2.5 | parts of isooctylphenoxy-polyoxyethylene-ethanol, |
| | 1.7 | parts of Champagne chalk/hydroxyethyl cellulose mixture (1:1), |
| | 8.3 | parts of sodium aluminum silicate, |
| | 16.5 | parts of kieselguhr, |
| | 46 | parts of kaolin; |
| e) | 10 | parts of Active Substance, |
| | 3 | parts of a mixture of the sodium salts of saturated fatty alcohol sulphates, |
| | 5 | parts of naphthalenesulphonic acid/formaldehyde condensate, |
| | 82 | parts of kaolin. |

The active substances are intimately mixed in suitable mixers with the additives, and the mixture is then ground in appropriate mills and rollers. Wettable powders are obtained having excellent wetting and suspension properties, which powders can be diluted with water to give suspensions of the desired concentration and which can be used, in particular, for leaf application.

Emulsifiable concentrates

The following substances are used to produce a 25% emulsifiable concentrate:

25 parts of Active Substance,
2.5 parts of epoxidised vegetable oil, 10 parts of an alkylarylsulphonate/fatty alcohol polyglycol ether mixture,
5 parts of dimethylformamide,
57.5 parts of xylene.

It is possible to produce from this concentrate, by dilution with water, emulsions of the desired concentration, which are particularly suitable for leaf application.

The following Examples serve to further illustrate the invention without limiting the scope thereof. Temperatures are given in degrees Centigrade.

EXAMPLE 1 (Compound No. 1.10)

Production of N-(2,6-dichloropyridine-4-carboxylic acid)N'-sec-butyl-hydrazide of the formula:

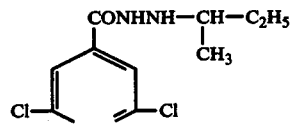

26.0 g of 2,6-dichloropyridine-4-carboxylic acid-2'-butylidene-hydrazone were dissolved in
260 ml of glycol monomethyl ether;
1.3 g of a 5% platinum-charcoal catalyst were added, and the solution was hydrogenated at 15°–20° until the reaction ceased. The reaction solution was filtered. concentrated in vacuo to dryness, and the crystallised residue recrystallised from ethyl acetate/ligroin to obtain colourless crystals, m.p. 110°–112°.

The same product may also be obtained in a known manner by reaction of 2,6-dichloropyridine-4-carboxylic acid methyl ester with a corresponding amount of 2-sec-butyl-hydrazine in ethanol, with refluxing being maintained for 4 hours.

The following compounds are produced in an analogous manner and/or by one of the methods described herein:

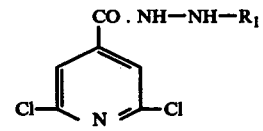

| Comp. No. | $R_1$ | Physical data |
|---|---|---|
| 1.11 | $-_nC_4H_9$ | b.p. 175–180/0,02 Torr. |
| 1.12 | $-C_2H_5$ | m.p. 115–120° |
| 1.13 | $-_nC_3H_7$ | m.p. 134–139° |
| 1.14 | $-_iC_3H_7$ | m.p. 131–133° |
| 1.15 | $-_iC_4H_9 \cdot HCl$ | m.p. 205–207° |
| 1.16 | $CH_3$ | m.p. 149–151° |

EXAMPLE 2 (Compound No. 2.10)

Production of N-(2,6-dichloropyridine-4-carbonyl)-N'-trichloroacetyl-hydrazide of the formula

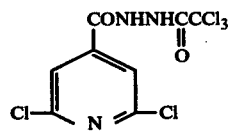

To a solution of 20.6 g of 2,6-dichloropyridine-4-carboxylic acid hydrazide (0.1 mole) and
12.0 g of triethylamine (0.12 mole) in
200 ml of abs. dioxane there were added dropwise at 20°–25°
19.2 g of trichloroacetyl chloride (0.106 mole), dissolved in
20 ml of abs. dioxane, and the reaction solution was stirred for 20 hours. The solution filtered off from the triethylamine-chlorohydrate was concentrated in vacuo. The yellowish oily residue was taken up in ether and washed with water, 5% sodium bicarbonate solution and again with water. The crystallised ether residue was recrystallised from toluene, m.p. 175°–178°.

The following compounds were produced in an analogous manner and/or by one of the methods described herein.

| Comp. No. | $R_1$ | Physical data |
|---|---|---|
| 2.11 | $-CO-C_4H_9(t)$ | m.p. 185–188° |
| 2.12 | $-CO-CH_3$ | m.p. 185–187° |
| 2.13 | $-CO-CH_2-Cl$ | m.p. 198–207° |
| 2.14 | $-CO-C_4H_9(i)$ | m.p. 208–210° |
| 2.15 | $-CO-C_3H_7(n)$ | m.p. 199–201° |
| 2.16 | $-CO-CH_2CH_2Br$ | m.p. |

EXAMPLE 3

Action against *Pseudomonas lachrymans* on cucumbers and against *Xanthomonas vesicatoria* on paprika

(a) Residual action (R)

Young cucumber and paprika plants were sprayed until dripping wet with the active substance in the form of a spray liquor with a content of active substance of 1000 ppm. One day after this application, the plants were infested by spraying of the underside of the primary leaves with suspensions of the respective bacteria, and then incubated for 8 days at 22° C. with 95% relative humdity. An evaluation was made after this period of time on the basis of the number of typical disease spots.

(b) Systemic action (S)

Young cucumber and paprika plants were watered with the active substance in the form of a suspension of the active substance (concentration 100 ppm relative to the pot soil). One day after this application, the plants were infested by spraying of the underside of the primary leaves with suspensions of the respective bacteria, and incubation was subsequently carried out for 8 days at 22° C. with 95% relative humidity. After this period of time, the evaluation was made on the basis of the number of typical disease spots. The following pyridine-4-carboxylic acid derivatives exhibited in the case of the stated bacteria a good action (i.e. plants less than 20% infested compared with untreated but infested control plants).

| Compound No. | Pseudomonas lachrymans R | S | Xanthomonas vesicatoria R | S |
|---|---|---|---|---|
| 1.10 | + |   | + | + |
| 1.11 | + | + |   | + |
| 1.12 | + |   | + | + |
| 1.13 | + |   | + |   |
| 1.14 | + | + | + | + |
| 1.15 | + | + | + | + |
| 2.10 | + | + | + | + |
| 2.11 | + | + | + | + |
| 2.12 |   | + | + | + |
| 2.13 |   | + | + | + |
| 2.14 |   | + | + | + |

EXAMPLE 5

Action against Venturia inaequalis on *Malus sylvestris*

Apple cuttings having fresh shoots 10–20 cm long were sprayed with a spray liquor (0.06% of active substance) produced from a wettable powder of the active substance. The treated plants were sprayed after 24 hours with a conidiospore suspension of the fungus. The plants were then subjected to an incubation treatment for 5 days at 90–100% relative humidity, and were afterwards left to stand for a further 10 days in a greenhouse at 20°–24° C. The scab infestation was assessed 15 days after infestation. The compound 1.10 exhibited in this test a good action (less than 20% infestation compared with untreated but infested control plants).

EXAMPLE 6

Growth inhibition in the case of grasses (post-emergence treatment)

Seeds of the grasses Lolium perenne, Poa pratensis, Festuca ovina and Dactylis glomerata were sown in plastic trays containing a soil/peat/sand mixture and normally watered. The emerged grasses were cut back each week to a height of 4 cm, and 40 days after sowing and one day after the last cutting they were sprayed with aqueous spray liquors of the active substances of formula I. The amount of active substance was equivalent to 5 kg of active substance per hectare. The growth of the grasses was evaluated 10 and 21 days after application on the basis of the following ratings:

1 = complete growth inhibition (no further growth after point of time of application),
9 = no inhibition (growth as in the case of the untreated control grasses).

The compound 1.15 attained for the various grasses ratings of between 1 and 4 (= severe growth inhibition).

We claim:

1. Compounds of the formula I

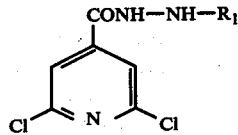

wherein
$R_1$ represents $C_1$–$C_4$-alkyl, alkyl($C_1$–$C_4$)-carbonyl or halogenoalkyl($C_1$–$C_3$)-carbonyl as well as salts thereof with organic and inorganic acids.

2. A compound according to claim 1 which is N-(2,6-dichloropyridine-4-carboxylic acid)-N'-sec-butyl hydrazide.

3. A compound according to claim 1 which is N-(2,6-dichloropyridine-4-carboxylic acid)-N'-trichloroacetyl-hydrazide.

4. A compound according to claim 1 which is N-(2,6-dichloropyridine-4-carboxylic acid)-N'-isobutylcarbonyl-hydrazide.

5. A microbicidal and plant-growth regulating composition comprising as active substance an amount effective for one or both of said purposes of a compound as claimed in claim 1 together with a suitable carrier therefor.

6. A microbicidal and plant-growth regulating composition comprising as active substance an amount effective for one or both of said purposes of a compound as claimed in claim 2 together with a suitable carrier therefor.

7. A microbicidal and plant-growth regulating composition comprising as active substance an amount effective for one or both of said purposes of a compound as claimed in claim 3 together with a suitable carrier therefor.

8. A microbicidal and plant-growth regulating composition comprising as active substance an amount effective for one or both of said purposes of a compound as claimed in claim 4 together with a suitable carrier therefor.

9. A method for combatting phytopathogenic microorganisms which comprises applying thereto or to the locus thereof a microbicidally effective amount of a compound as claimed in claim 1.

10. A method for combatting phytopathogenic microorganisms which comprises applying thereto or to the locus thereof a microbicidally effective amount of a compound as claimed in claim 2.

11. A method for combatting phytopathogenic microorganisms which comprises applying thereto or to the locus thereof a microbicidally effective amount of a compound as claimed in claim 3.

12. A method for combatting phytopathogenic microorganisms which comprises applying thereto or to the locus thereof a microbicidally effective amount of a compound as claimed in claim 4.

13. A method for advantageously regulating plant growth which comprises applying thereto or to the locus thereof an amount effective in regulating plant growth of a compound as claimed in claim 1.

14. A method for advantageously regulating plant growth which comprises applying thereto or to the lucus thereof an amount effective in regulating plant growth of a compound as claimed in claim 2.

15. A method as claimed in claim 9 wherein the microorganisms to be combatted are phytopathogenic bacteria.

16. A method as claimed in claim 10 wherein the microorganisms to be combatted are phytopathogenic bacteria.

17. A method as claimed in claim 11 wherein the microorganisms to be combatted are phytopathogenic bacteria.

18. A method as claimed in claim 12 wherein the microorganisms to be combatted are phytopathogenic bacteria.

* * * * *